United States Patent [19]
Graham et al.

[11] Patent Number: 5,595,996
[45] Date of Patent: Jan. 21, 1997

[54] 7-SUBSTITUTED 4-AZA CHOLANIC ACID DERIVATIVES AND THEIR USE

[75] Inventors: Donald W. Graham, Mountainside; Josephine R. Carlin, New Brunswick; Shuet-Hing L. Chiu, Westfield; Richard L. Tolman, Warren, all of N.J.

[73] Assignee: Merck & Co., Inc., Rahway, N.J.

[21] Appl. No.: 328,622

[22] Filed: Oct. 25, 1994

[51] Int. Cl.$^6$ .................... A61K 31/44; C07D 221/18; C07D 221/04
[52] U.S. Cl. .................... 514/284; 546/77; 546/159; 546/285; 562/499; 549/69; 549/480; 548/557
[58] Field of Search .................... 546/77; 514/284

[56] References Cited

U.S. PATENT DOCUMENTS

| | | | |
|---|---|---|---|
| 5,215,894 | 6/1993 | Arison et al. | 435/53 |
| 5,304,562 | 4/1994 | Biollaz | 514/284 |
| 5,359,071 | 10/1994 | Durette et al. | 546/78 |
| 5,378,710 | 1/1995 | Biollaz | 514/284 |
| 5,418,238 | 5/1995 | Panzeri et al. | 514/284 |

*Primary Examiner*—Alan L. Rotman
*Attorney, Agent, or Firm*—Catherine D. Fitch; Joanne M. Giesser; Melvin Winokur

[57] ABSTRACT

Compounds of the Formula I

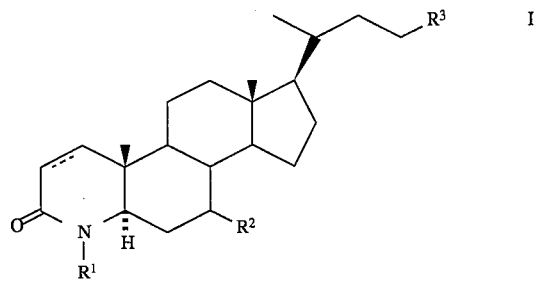

wherein: the dotted line indicates that a double bond may be present or absent; $R^1$ is H, methyl or ethyl; $R^2$ is α- or β-$C_{1-10}$ straight or branched alkyl; $R^3$ is $CO_2H$, CN, $CO_2R^4$, $COHNR^4$, or $CON(R^4)_2$; $R^4$ is H, $C_{1-10}$ straight or branched alkyl, aryl, heteroaryl, or aralkyl; Aryl is phenyl, substituted phenyl, naphthyl, or biphenyl; Heteroaryl is pyridyl, pyrrolyl, thienyl, furanyl or quinolinyl; and Aralkyl is $C_{1-10}$alkyl substituted with one to three phenyl or substituted phenyl moieties; and their pharmaceutically acceptable salts are described. These compounds are 5α-reductase type 1 inhibitors. They may be used for treating conditions associated with an excess of DHT, either alone or in combination with other 5α-reductase inhibitors.

9 Claims, No Drawings

7-SUBSTITUTED 4-AZA CHOLANIC ACID DERIVATIVES AND THEIR USE

DESCRIPTION OF THE INVENTION

This invention relates to novel 7-substituted 4-aza cholanic acid derivatives which are 5α-reductase inhibitors and their use in the treatment of various disorders associated with an excess of 5α-reductase.

BACKGROUND OF THE INVENTION

Certain undesirable physiological conditions, including acne vulgaris, seborrhea, female hirsutism, male pattern baldness, benign prostatic hyperplasia and prostatic cancer can be the result of hyperandrogenic stimulation caused by an excessive accumulation of testosterone or similar androgenic hormones in the metabolic system. Early attempts to provide a chemotherapeutic agent to counter the undesirable effects of hyperandrogenicity resulted in the discovery of several steroidal antiandrogens having undesirable hormonal activities of their own. The estrogens, for example, not only counteract the effect of the androgens, but have a feminizing effect as well. Nonsteroidal antiandrogens have also been developed, such as 4'-nitro-3'-trifluoromethyl-isobutyranilide, such as described in Neri et al., *Endocrinology*, 91, No. 2 (1972). However, these products, though devoid of hormonal effects, compete with all natural androgens for receptor sites, and hence have a tendency to feminize a male host or the male fetus of a female host and/or initiate feed-back effects which would cause hyperstimulation of the testes.

It is now known that the principal mediator of androgenic activity in some target organs, e.g., the prostate is 5α-dihydrotestosterone (DHT), and that it is formed locally in the target organ by the action of testosterone-5α-reductase. It is also known that inhibitors of testosterone-5α-reductase can prevent or lessen the symptoms of hyperandrogenetic stimulation.

A number of 4-aza steroid compounds are known which are 5α-reductase inhibitors. See the following Merck & Co., Inc. patents: U.S. Pat. Nos. 4,377,584, 4,220,775, 4,859,681, and 4,760,071. See also Rasmusson et al., 1984, *J. Med. Chem.*, 27:1690–1701) and Rasmusson et al., 1986, *J. Med. Chem.*, 29:2998–2315, and EP Publication 0 484 094 to Sankyo, which describe 4-aza-17β-substituted 5α-androstan-3-ones said to be useful in the treatment of DHT-related hyperandrogenic conditions.

Recently, Anderson and Russell isolated a cDNA which encodes a rat liver 5α-reductase (see *J. Biol. Chem.*, 264:16249–55, 1989). They found that a single mRNA which encodes both the liver and prostatic reductases of rats. The sequence of this rat gene was later used to select a human prostatic cDNA encoding a 5α-reductase termed "5α-reductase 1" (*Proc. Natl. Sci. USA*, 87:3640–3644, 1990). More recently, a second human prostatic reductase (5α-reductase 2) has been cloned with properties identified with the more abundant form found in crude prostatic extracts (see Nature, 354:159–161, 1991).

Thus, there are at least two genes for 5α-reductase and two distinct isozymes of 5α-reductase in humans. While both forms are present in prostatic tissue, 5α-reductase 2 is more abundant there. The other isozyme, 5α-reductase 1 is believed to be more abundant in scalp and skin tissue.

In the treatment of hyperandrogenetic disease conditions, it would be desirable to have one drug entity which is highly selective for inhibiting the scalp and skin associated enzyme 5α-reductase 1 for the use in treating diseases of the skin and scalp, such as acne and alopecia.

DESCRIPTION OF THE INVENTION

This invention related to the compounds of the Formula I

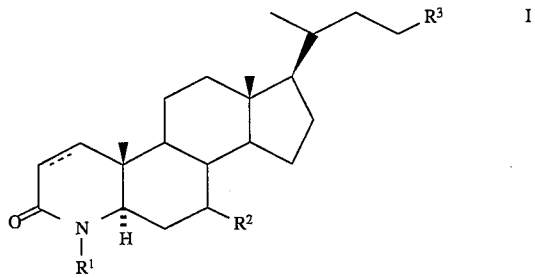

wherein:
the dotted line indicates that a double bond may be present or absent;

$R^1$ is H, methyl or ethyl;

$R^2$ is α- or β-$C_{1-10}$ straight or branched alkyl;

$R^3$ is $CO_2H$, CN, $CO_2R^4$, $COHNR^4$, or $CON(R^4)_2$, or $CONH(CH_2)_2SO_3H$;

$R^4$ is H, $C_{1-10}$ straight or branched alkyl, aryl, heteroaryl, or aralkyl;

Aryl is phenyl, substituted phenyl, naphthyl, or biphenyl;

Heteroaryl is pyridyl, thiazolyl, thienyl, furanyl or quinolinyl; and

Aralkyl is $C_{1-10}$alkyl substituted with one to three phenyl or substituted phenyl moieties;

or a pharmaceutically acceptable salt thereof.

"Substituted phenyl" is a phenyl substituted by one or more $C_{1-2}$ alkyl substituents and/or by one or more halo (Cl, Br, F) substituents.

The compounds of Formula I are potent inhibitors of the 5α-reductase type 1 isoenzyme, primarily associated with the skin and scalp tissues. As such, they are useful for treatment of disorders of the skin and scalp which are related to an excess of DHT, including androgenic alopecia, acne vulgaris, female hirsutism, and seborrhea. Further, they are useful in lowering serum DHT levels in general and may be used either alone or in conjunction with a specific 5α-reductase type 2 inhibitor for treatments related to an excess of DHT, including benign prostatic hyperplasia (BPH), and the treatment and/or prevention of prostatic cancer. In particular, they may be used in combination with finasteride (sold under the trademark PROSCAR®) for treatment of acne vulgaris, and BPH, or for the prevention and treatment of prostatic cancer. Another preferred use is in combination with another 5α-reductase type 1 inhibitor for conditions which affect the skin and scalp, and/or for a general lowering of serum DHT.

The substituent at position 7 may be either in the α- or β-configuration. The substituent at position 20 may be in either the 20-R or 20-S configuration; 20-S is preferred.

Representative preferred compounds of this invention include:
7-methyl-3-oxo-4-aza-5α-cholan-24-oic acid,
4,7-dimethyl-3-oxo-N-(2-sulfoethyl)-4-aza-5α-cholan-24-amide,
7-methyl-3-oxo-4-aza-5α-chol-1-en-24-oic acid,
7-ethyl-3-oxo-4-aza-5α-chol-1-en-24-oic acid,
4,7-dimethyl-3-oxo-4-aza-5α-cholan-24-oic acid,
4-ethyl-7-methyl-3-oxo-4-aza-5α-chol-24-oic acid, phenyl 7-methyl-3-oxo-4-aza-5α-cholan-24-oate,
4,7-dimethyl-3-oxo-4-aza-5α-cholano-24-nitrile,
4,7-dimethyl-3-oxo-N-phenyl-4-aza-5α-cholan-24-amide,
4,7-dimethyl-3-oxo-4-aza-5α-cholan-24-amide,
7-methyl-3-oxo-4-aza-5α-chol-1-en-24-amide,
N,N-diethyl-4,7-dimethyl-3-oxo-4-aza-5α-cholan-24-amide,
N-(1,1-dimethylethyl)-4,7-dimethyl-3-oxo-4-aza-5α-cholan-24-amide,
4-methyl-7-(n-pentyl)-3-oxo-4-aza-5α-cholano-24-nitrile,
4-methyl-7-(n-decyl)-3-oxo-4-aza-5α-cholano-24-nitrile,
4,7-dimethyl-N-(diphenylmethyl)-3-oxo-4-aza-5α-cholan-24-amide,
7-methyl-3-oxo-N-(4-pyridyl)-4-aza-5α-chol-1-en-24-amide,
2-methoxyphenyl 4,7-dimethyl-3-oxo-4-aza-5α-cholan-24-oate,
4,7-dimethyl-3-oxo-N-(1,1,3,3-tetramethylbutyl)-4-aza-5α-cholan-24-amide,
N-(4-acetylphenyl)-4,7-dimethyl-3-oxo-4-aza-5α-cholan-24-amide,
1,1-dimethylethyl 7-methyl-3-oxo-4-aza-5α-chol-1-en-24-oate,
4,7-dimethyl-N,N-dioctyl-3-oxo-4-aza-5α-cholan-24-amide,
4,7-dimethyl-3-oxo-N-(2-thiazolyl)-4-aza-5α-cholan-24-amide,
4,7-dimethyl-3-oxo-N-(4-phenylbutyl)-4-aza-5α-cholan-24-amide.

Thus another aspect of this invention includes the prevention or treatment of a condition related to an excess of DHT, said condition selected from the group consisting of: androgenic alopecia, acne vulgaris, seborrhea, female hirsutism, benign prostatic hyperplasia, prostatitis, and prostatic cancer comprising the step of administering to an animal a therapeutically effective or prophylactically effective amount of a compound of Formula I.

The term "pharmaceutically acceptable salt" is intended to include all acceptable salts, such as hydrochloride, hydrobromide, acetate, pamoate and the like which can be used as a dosage form for modifying solubility or hydrolysis characteristics or can be used in sustained release or pro-drug formulations.

The present invention also includes pharmaceutical compositions comprising a compound of Formula I in a pharmaceutically acceptable carrier. Such formulations may be suitable for topical, oral or parenteral use in the treatment or prevention of conditions associated with an excess of DHT.

The compositions containing the compounds of the present invention as the active ingredient for use in the treatment of benign prostatic hypertrophy, prostatitis, and prostatic carcinoma can be administered in a wide variety of therapeutic dosage forms in convenient vehicles for systemic administration, as, for example, by oral administration in the form of tablets, capsules, solution, or suspension, or by intravenous or intramuscular injection or by subdermal implantation. The dosage of the products for an adult human can be varied over a wide range varying from 0.1 to 1,000 mg per day. The compositions are preferably in the form of scored tablets containing 0.1, 0.5, 1.0, 2.5, 5.0, 10.0, 15.0, 25.0 or 50.0 milligrams of active ingredient for the symptomatic adjustment of the dosage to the patient to be treated. An effective amount of the drug is ordinarily supplied at a dosage level of from about 0.002 mg to about 50 mg/kg of body weight per day. Preferably the range is from about 0.01 mg to 7 mg/kg of body weight per day. These dosages are well below the toxic dose of the product.

Capsules containing the product of this invention can be prepared by mixing an active compound of the present invention with lactose and magnesium stearate, calcium stearate, starch, talc, or other carriers, and placing the mixture in a gelatin capsule. Tablets may be prepared by mixing the active ingredient with conventional tableting ingredients such as calcium phosphate, lactose, cornstarch or magnesium stearate. The liquid forms in suitable flavored suspending or dispersing agents such as the synthetic and natural gums, for example, tragacanth, acacia, methyl-cellulose and the like. Other dispersing agents which can be employed include glycerin and the like. For parenteral administration, suitably prepared implants or sterile suspensions and solutions are desired. Isotonic preparations which generally contain suitable preservative(s) are typically employed when intravenous administration is desired.

For the treatment of acne vulgaris, seborrhea, female hirsutism, and androgenic alopecia, the compounds of the present invention can be administered in the form of pharmaceutical composition comprising the active compound in combination with a pharmacologically acceptable carrier adapted for topical administration, although parenteral or oral administration is also applicable. These topical pharmaceutical compositions can be in the form of a cream, ointment, gel or aerosol formulation adapted for skin application. These topical pharmaceutical compositions containing the compounds of the present invention ordinarily include about 0.1% to 15%, preferably about 2–5% of the active compound admixture, with the remaining 98-95% being vehicle. They may be administered alone or in combination with other active ingredients, including other 5α-reductase type 1 or type 2 inhibitors.

When prophylaxis or therapy is to be achieved by the use of a compound of this invention in combination with another active ingredient, the term "administration" or grammatical forms thereof is intended to include both the administration of both concurrently and the administration of each agent in a staggered fashion.

The pharmaceutical compositions included herein include those comprising a pharmaceutically acceptable carrier and a therapeutically effective amount of a compound of Formula I which can further contain:

1) a therapeutically effective amount of an inhibitor of 5α-reductase 2, or a pharmaceutically acceptable salt thereof, e.g., finasteride, epristeride (WO91/13550), or turosteride (U.S. Pat. No. 5,155,107);

2) a potassium channel opener, or a pharmaceutically acceptable salt thereof; e.g., minoxidil cromakalin, or pinacidil;

3) a therapeutically effective amount of a retinoid, or a pharmaceutically acceptable salt thereof, e.g., tretinoin (RETINA), isotretinoin (ACCUTANE);

4) a therapeutically effective amount of an anti-androgen, or pharmaceutically acceptable salt thereof, e.g., flutamide, speronolactone or casodex;

5) a therapeutically effective amount of an alpha-1 receptor antagonist, e.g., terazosin (U.S. Pat. No. 4,026,894); or 6) a therapeutically effective amount of an antibacterial agent, an antiinflarmnatory agent and/or a keratolytic agent.

The compounds of Formula I may be synthesized chemically, as set forth below, or they may be isolated from various tissues, feces, and urine as metabolites of the 5α-reductase type 1 inhibitors 4,7β-dimethyl-4-aza-5α-cholestan-3-one and similar compounds. Thus another aspect of this invention is a method of administering a compound of Formula I comprising administering 4,7β-dimethyl- 4-aza-5α-cholestan-3-one and similar compounds, and isolating, if desired. Yet another aspect of this invention is a pharmaceutical composition comprising compounds of Formula I and another 5α-reductase type 1 inhibitor, and preferably 4,7β-dimethyl-4-aza-5α-cholestan-3-one or similar compounds. Such compounds are described in the PCT publication WO93/23419, published Dec. 25, 1993, which is hereby incorporated by reference.

A synthetic procedure for production of compounds of the Formula I is shown below.

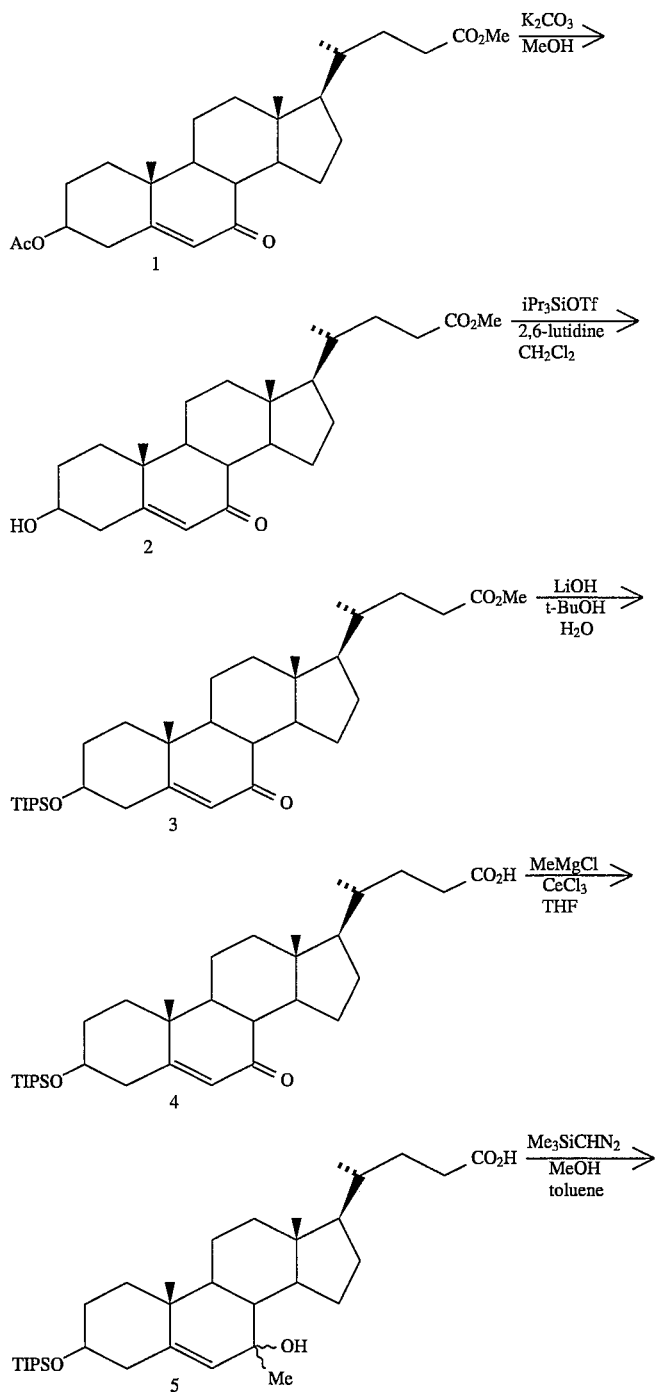

-continued
SCHEME 1
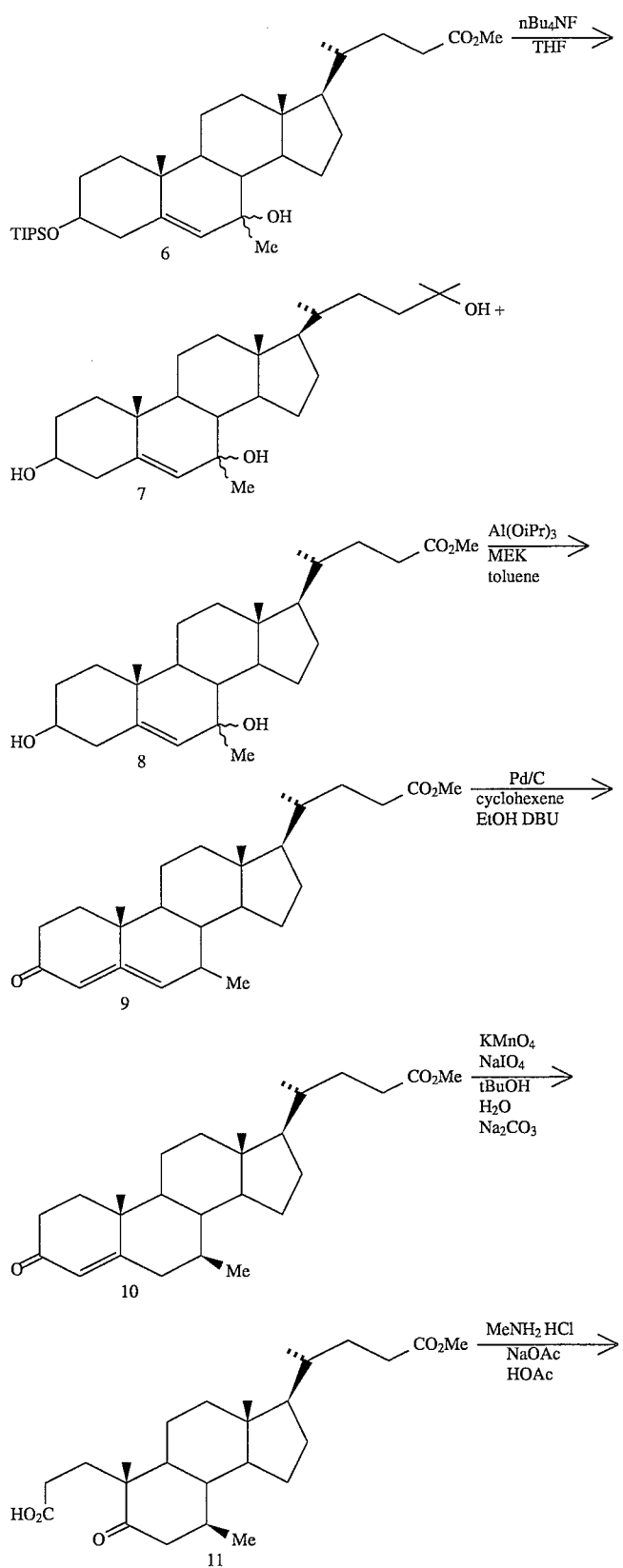

-continued
SCHEME 1

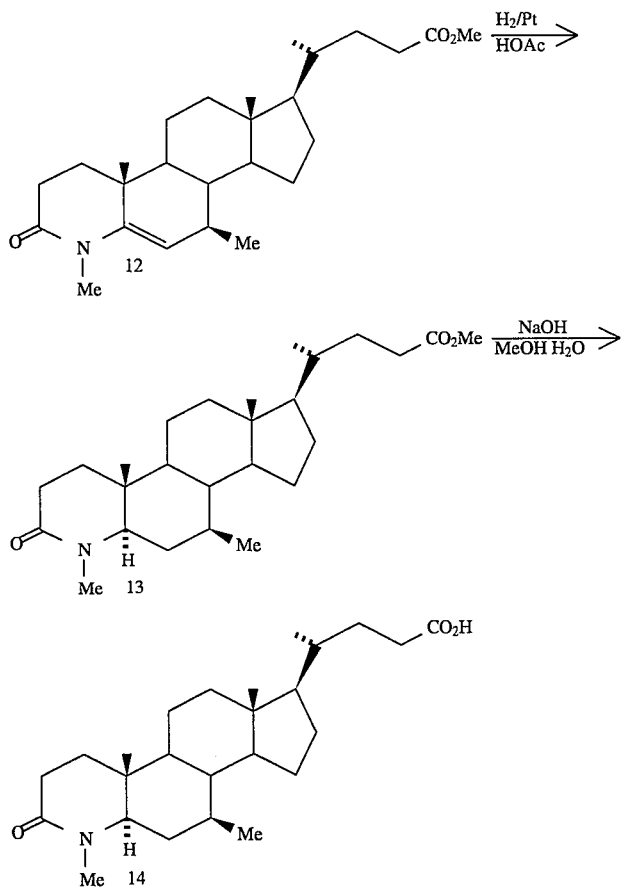

The starting material (1) is known and is described in Norii et al., 1970, Steroids, 15:303, which is hereby incorporated by reference. First, the acetate starting material is subjected to a hydrolysis using a mild base such as $K_2CO_3$ in MeOH to retain the $CO_2Me$ group. Next, the resulting —OH moiety at position 3 is protected with a silyl protecting group. An example of an appropriate silyl protecting group is triisopropylsilyl, but other such groups having similar functions such a t-butyldimethylsilyl, phenyl-dimethysilyl or tetrahydropyranyl may also be employed. The triisopropylsilyloxy compound (2) may be prepared with triisopropylsilyl trifluormethylsulfonate and 2,6-lutidine in methylene chloride. Other silylating conditions such as triisopropylsilylchloride and imidazole could be employed. The resulting methyl ester (3) is then saponified using a base such as LiOH, although other bases such as NaOH and KOH may also be employed. Preferred solvents include t-butyl alcohol or isopropanol, as they help to prevent any addition to the 5-en-7-one system from occurring. The next step involves a Grignard-type addition to the 6-ketone, preferably using methyl magnesium chloride in THF mediated by cesium trichloride, although methyl magnesium bromide or iodide in ether may be substituted. A mixture of compounds are formed: 24-carboxylic acids (7) and compounds having a tertiary alcohol group at position 24. These need not separated at this point, but will preferably be separated in a subsequent step. In addition, the carboxylic acids exist in two isomeric forms with respect to the 7-position moieties (at approximately a 1:1 ratio). There is no need to separate the isomers. The carboxylic acid isomers are then esterified using trimethylsilyldiazomethane, although diazomethane could be used. The resulting methyl esters (6) are deprotected at position 3 using tetrabutyl ammonium fluoride to give the 3-hydroxy compounds. The resulting compounds, a 24-tertiary alcohol (7) and the 24-methyl ester in two isomeric forms (8) are separated, and the synthesis continues with the latter. The 24-methyl ester is subjected to an Oppenhauer oxidation s reaction using aluminum isopropoxide and methyl ethyl ketone in toluene. Other ketones such as cyclohexanone can be used. This reaction oxidizes the 3-hydroxy and also dehydrates position 7, resulting in the dienone (9). The dienone is then reduced to the 7β-methyl compound (10) stereospecifically with a transfer hydrogenation process using a palladium on carbon catalyst and cyclohexene as the hydrogen donor in the presence of 1,8-diazobicyclo[5.4.0]-undec-7-ene (DBU), a strong base used to isomerize the double bond into the 4-position. Other catalysts including platinum on carbon, palladium, or platinum alone and other hydrogen donors such as 1,3- or 1,4-cyclohexadiene also may be used.

In the next step, the enone (10) is oxidized to the seco acid (11) using standard oxidation reagents: sodium periodate with a catalytic amount of potassium permanganate in aqueous t-butanol. Ozonization in methylene chloride-methanol followed by aqueous sodium hydroxide may also be used. The ring is then closed to produce the Δ5-azasteroid (12). While $MeNH_2$ is a preferred reactant, other amines or amine hydrochlorides in the presence of acetates can also be used. The Δ5-azasteroid is hydrogenated to make the 5α-azasteroid (13). Platinum catalyst in an acetic acid solvent is preferred to give the highest yield of the 5α-stereoisomer, but palladium in ethanol or methanol solvent may also be used. In the final step, saponification and acidification gives the 24-carboxylic acid (14).

While the foregoing presents one scheme for synthesizing a particular compound, it is well within the skill of the ordinary artisan to modify the above reaction scheme using known processes and reactants to create other compounds embraced by Formula I. For example, treating the seco acid (11) with ammonium chloride and sodium acetate rather than methylamine hydrochloride-sodium acetate, then saponifying the resultant 4-H analog of ester (13) will result in the 4-H analog of compound (14). For compounds where $R^1$ is ethyl, ethylamine.HCl can be used in the reaction with the seco acid.

The above 4-H analog of ester (13) can be reacted with s 2,3-dichloro-5,6-dicyanobenzoquinone using the procedure of Dolling, et al., 1988 *J. Amer. Chem. Soc.*, 110:3318–3319, which is hereby incorporated by reference, to give the $\Delta^1$-4-H analog of ester (13). Saponification and acidification would give the $\Delta^1$-4-H analog of carboxylic acid (14).

For compounds where $R^2$ is an alkyl other than methyl, the Grignard reagent which is reacted with (4) should be changed to an appropriate magnesium chloride derivative such as ethyl-, n-propyl-, isopropyl- or decyl- MgCl.

For compounds where $R^3$ is COHNR$^4$, compound (14) may be reacted with a corresponding amine, such as $NH_3$, diethylamine, methylamine, dimethylamine, dioctylylamine, tert-butylamine, aniline, para-chloroamine, 2-aminopyridine, 4-aminobiphenyl, benzylamine, diphenylmethylamine, 2-aminothiazole, 2-aminofuran, 2-aminnoquinoline, 4-aminopyridine, or the like, using such common amide forming reagents as dicyclohexylcarbodiimide, 1-(3-dimethylaminopropyl)-3-ethylcarbodiimide hydrochloride, or N,N-bis[2-oxo-3-oxazolidinyl]-phosphorinic chloride. Alternatively, the carboxylic acid (14) can be converted into the acid chloride with thionyl cloride or oxalyl choride, and the acid chloride reacted with the appropriate amine in the presence of a catalyst such as 4-dimethylaminopyridine.

The analog where $R^3$ is —CN may be formed from primary amide ($R^3$ is $CONH_2$) by dehydration using either $POCl_3$ or $P_2O_5$.

When $R^3$ is $CO_2R^4$, the carboxylic acid such as (14) may be reacted with an alcohol such as tert-butanol, isopropanol, n-hexanol, phenol, 2-methoxyphenol, 2-hydroxypyridine or 2-hydroxyquinoline, using ester forming reagents such as dicyclohexylcarbodiimide or 1-(3-dimethylaminopropyl)-3-ethylcarbodiimide hydrochloride. Alternatively, the carboxylic acid (14) can be converted to the acid chloride with thionyl chloride or oxalyl chloride, and the acid chloride reacted with the appropriate alcohol in the presence of a catalyst such as 4-dimethylaminopyridine.

The following non-limiting Examples are presented to better illustrate the invention.

EXAMPLE 1

Preparation of methyl 3β-hydroxy-7-oxochol-5-en-24-oate (2)

To a suspension of finely ground $K_2CO_3$ (3.45 g, 25 mmoles) in 250 ml of methanol was added methyl 3β-acetoxy-7-oxochol-5-en-24-oate (1) (11.1 g, 25 mmoles). After stirring at 45° for 15 minutes in a $N_2$ atmosphere, most of the methanol was removed in vacuo from the clear brown reaction mixture. The residue was suspended in $H_2O$ and extracted three times with $CH_2Cl_2$. The combined extracts were washed with H20 twice and saturated brine and dried with $MgSO_4$. Evaporation in vacuo gave 10.1 g of nearly pure 2 as a pale yellow solid. The nuclear magnetic resonance data for this and subsequent Examples was taken at 400 MHz in $CDCl_3$: δ0.68 (s, 3H, 18-Me); 0.94 (d, 3H, 20-Me); 1.21 (s, 3H, 19-Me); 3.66 (s, 3H, $CO_2Me$); 3.68 (m, 1H, 3-H); 5.70 (s, 1H, 6-H).

EXAMPLE 2

Preparation of methyl 7-oxo-3β-triisopropylsilyloxychol-5-en-24-oate (3)

To a solution of methyl 313-hydroxy-7-oxochol-5-en-24-oate (2) (5.02 g, 12.5 mmoles) and 2,6-1utidine (3.32 ml, 28.5 mmoles) in $CH_2Cl_2$ (23 ml) cooled in an ice bath in a $N_2$ atmosphere was added dropwise with magnetic stirring triisopropylsilyl trifluoromethanesulfonate (4.56 g, 17 mmoles). After 2 hrs, the reaction was diluted with $CH_2Cl_2$ (150 ml). It was then washed with cold 2N HCl, washed twice with $H_2O$ and then with saturated brine before drying with $MgSO_4$. Evaporation in vacuo and purification of the residue by flash chromatography on silica gel with hexane-EtOAc (10:1 ) gave 5.88 g of 3 as a colorless syrup. NMR ($CDCl_3$): δ0.67 (s, 3H, 18-Me); 0.93 (d, 3H, 20-Me); 1.06 (s, 18H, TIPS Me); 1.19 (s, 3H, 19-Me); 3.66 (s, 3H, $CO_2Me$); 3.68 (m, 1H, 3-H); 5.66 (s, 1H, 6-H).

EXAMPLE 3

Preparation of 7-oxo-3β-triisopropylsilyloxychol-5-en-24-oic acid (4)

Methyl 7-oxo-3β-triisopropylsilyloxychol-5-en-24-oate (3) (5.85 g, 10.5 mmoles) was dissolved with warming in t-BuOH (100 ml). A solution of $LiOH.H_2O$ (1.76 g, 41.9 mmoles) in $H_2O$ (33 ml) was added, and the two phase mixture was heated at 80° with magnetic stirring in an $N_2$ atmosphere for 2 hrs. Most of the t-BuOH was evaporated in vacuo, the residue-diluted with $H_2O$ (~50 ml), and acidified with 2N HCl (22 ml). The gummy suspension was extracted with $CH_2Cl_2$ (4 times). The extracts were washed with $H_2O$ and saturated brine and dried ($MgSO_4$). Evaporation in vacuo gave 5.38 g of 4 as a gummy solid. NMR ($CDCl_3$): δ0.68 (s, 3H, 18-Me); 0.95 (d, 3H, 20-Me); 1.05 (s, 18H, TIPS Me); 1.20 (s, 3H, 19-Me); 3.68 (m, 1H, 3-H); 5.67 (s, 1H, 6-H).

EXAMPLE 4

Preparation of 7-methyl-7-hydroxy-3β-triisopropylsilyloxychol-5-en-24-oic acid (5)

A suspension of anhydrous $CeCl_3$ (1.21 g, 4.94 mmoles) was stirred at room temperature in a $N_2$ atmosphere with dry THF (16.5 ml) for 2 hrs. MeMgCl (3N in THF, 16.5 ml) was added dropwise at room temperature, and the suspension was stirred from 30 minutes. A solution of 7-oxo-3β-triisopropylsilyloxychol-5-en-24-oic acid (4) (5.38 g, 9.9 mmoles) in dry THF (16.5 ml) was added dropwise over 20 minutes keeping the temperature of the reaction mixture below 20° with a cold $H_2O$ bath. After stirring at room temperature for 2 hrs, the reaction mixture was poured carefully with efficient stirring into a mixture of 90% saturated $NH_4Cl$ solution and 100 g of ice. The gummy suspension was acidified with 2N HCl, stirred well for 30 minutes and extracted with $CH_2Cl_2$ (three times). The combined s extracts were washed with $H_2O$ and saturated brine and dried ($MgSO_4$). Evaporation in vacuo gave 5.46 g of crude 5 as a tan foam. NMR ($CDCl_3$) indicated a mixture of 7-isomers: δ0.70 (two peaks, 18-Me); 5.14 & 5.20 (6-H) The mixture was used directly in the next reaction (Example 5).

EXAMPLE 5

Preparation of methyl 7-hydroxy-7-methyl-3β-triisopropylsilyloxy-chol-5-en-24-oate (6)

To a solution of 7-hydroxy-7-methyl-3β-triisopropylsilyl-oxychol-5-en-24-oic acid (5) (5.38 g, 9.68 mmoles) in toluene (70 ml) and methanol (20 ml) was added dropwise at room temperature trimethylsilyldiazomethane (2.0N in hexane, ~5 ml). After 30 minutes $N_2$ evolution ceased, and the reaction mixture was a pale yellow. The solvent was removed in vacuo to give 4.67 g of crude 6 as a brown syrup. NMR ($CDCl_3$) indicated a mixture of 7-isomers: δ0.69 (two peaks, 18-Me); 3.63 (s, $CO_2Me$); 5.12 & 5.18 (6-H). The mixture was used directly in the next reaction (Example 6).

EXAMPLE 6

Preparation of methyl 3β,7-dihydroxy-7-methylchol-5-en-24-oate

A mixture of methyl 7-hydroxy-7-methyl-3β-triisopropyl-silyloxychol-5-en-24-oate (6) (4.67 g, 8.22 mmoles) and tetrabutylammonium fluoride (1.0M in THF, 49 ml) was heated at 65° in a $N_2$ atmosphere for 30 minutes. Most of the THF was removed in vacuo. The residue was dissolved in EtOAc (90 ml) and washed with $H_2O$ (two times) and saturated brine. The aqueous phases were back-extracted with EtOAc. The combined EtOAc extracts were dried ($MgSO_4$). Evaporation in vacuo and flash chromatography on silica gel with 7% methanol-$CH_2Cl_2$ gave 2.08 g of 8 as a yellow-brown foam. NMR ($CDCl_3$) indicated a mixture of 7-isomers: δ0.70 (two peaks, 18-Me); 3.66 ($CO_2Me$). Further elution gave 0.50 g of the tertiary alcohol 7 as a mixture of 7-isomers. NMR ($CDCl_3$): δ0.70 (two peaks, 18-Me); 1.20 ($CMe_2OH$).

EXAMPLE 7

Preparation of methyl 7-methyl-3-oxochola-4,6-dien-24-oate (9)

A mixture of methyl 7-hydroxy-7-methylchol-5-en-24-oate (8) (2.0 g, 4.78 mmoles), aluminum isopropoxide (1.17 g, 5.72 mmoles), 2-butanone (8.6 ml, 96 mmoles) in toluene (40 ml) was heated at 80° in a $N_2$ atmosphere for 6 hrs. About 15 ml of solvent was distilled from the reaction mixture at atmospheric pressure. Toluene (30 ml) was added, and the mixture was extracted with 3N HCl (2 times), $H_2O$ (3 times) and dried with $MgSO_4$. Evaporation in vacuo gave 1.7 g of an orange oil that was purified by flash chromatography on silica gel with hexane-EtOAc (7:2 and 2:1 ) to give 0.62 g of pure 9 as a colorless syrup. NMR ($CDCl_3$): δ0.76 (s, 3H, 18-Me); 0.94 (d, 3H, 20-Me); 1.08 (s, 3H, 19-Me); 3.67 (s, 3H, $CO_2Me$); 5.59 (s, 1H, 4H); 5.95 (s, 1H, 6-H).

EXAMPLE 8

Preparation of methyl 7β-methyl-3-oxo-chol-4-en-24-oate (10)

A mixture of methyl 7-methyl-3-oxochola-4,6-dien-24-oate (9) (0.62 g, 1.56 mmoles), 5% palladium on carbon (72 mg), 1,8diazobicyclo-[5.4.0]undec-7-ene (15 gl), cyclohexene (4.9 ml) and ethanol (3.6 ml) was heated under reflux in an $N_2$ for 6 hrs. The cooled mixture was filtered, and the catalyst washed with ethanol (4 times). The combined filtrate and washes were evaporated in vacuo. The residue was dissolved in EtOAc (30 ml), washed with 0.5M HCl, $H_2O$, saturated brine and dried ($MgSO_4$). Evaporation in vacuo gave 0.62 g of pure 10 as a pale yellow syrup. NMR ($CDCl_3$): δ0.71 (s, 3H, 18-Me); 0.94 (d, 3H, 20-Me); 1.05 (d, 3H, 7-Me); 1.15 (s, 3H, 19-Me); 3.66 (s, 3H, $CO_2Me$); 5.70 (s, 1H, 4-H).

EXAMPLE 9

Preparation of 7β-methyl-5-oxo-A-nor-3,5-secocholan-3,24-dioic acid 24-methyl ester (11 )

A warm solution of $NaIO_4$ (2.30 g, 10.8 mmoles) and $KMnO_4$ (17 mg) in $H_2O$ (9 ml) was added over 20 minutes with magnetic stirring to a mixture of methyl 7β-methyl-3-oxo-chol-4-en-24-oate (10) (0.62 g, 1.55 mmoles), $Na_2CO_3$ (248 mg, 2.34 mmoles) in $H_2O$ (1.2 ml), and t-BuOH (9 ml) while the mixture was heated at 90°. The two-phase mixture was heated under reflux for 2 hrs. The cooled brown suspension was filtered through a bed of Celite which was washed with $H_2O$ (3 times). Most of the t-BuOH was removed from the filtrate and washes in vacuo. After extraction with EtOAc, the aqueous phase was acidified with 2N HCl and the cloudy suspension extracted with $CH_2Cl_2$ (4 times). The extracts were washed with $H_2O$ and dried ($MgSO_4$). Evaporation in vacuo gave 586 mg of 11 as a colorless syrup. NMR ($CDCl_3$): δ0.69 (s, 3H, 18-Me); 0.93 (d, 3H, 20-Me); 0.96 (d, 3H, 7-Me); 1.03 (s, 3H, 19-Me); 3.67 (s, 3H, $CO_2Me$).

EXAMPLE 10

Preparation of methyl 4,7β-dimethyl-3-oxo-4-azachol-5-en-24-oate (12)

A mixture of 7β-methyl-5-oxo-A-nor-3,5-secocholan-3, 24-dioic acid 24-methyl ester (11) (88 mg, 0.21 mmoles), $MeNH_2.HCl$ (71 mg, 1.05 mmoles); NaOAc (86 mg, 1.05 mmoles) in HOAc (0.5 ml) was heated at 130° in a $N_2$ atmosphere with magnetic stirring for 2 hrs. The cooled reaction was poured onto excess 10% $Na_2CO_3$, and extracted with $CH_2Cl_2$ (3 times). The combined extracts were washed with $H_2O$ and dried ($MgSO_4$). Evaporation in vacuo and purification by preparative TLC on silica gel with 7% MeOH in $CH_2Cl_2$ gave 12. NMR ($CDCl_3$): δ0.71 (s, 3H,18-Me); 0.95 (d, 3H, 20-Me); 1.01 (s, 3H, 19-Me); 1.07 (d, 3H, 7-Me); 3.14 (s, 3H, 4-Me); 3.67 (s, 3H, $CO_2Me$); 4.84 (d, 1H, 6-H).

EXAMPLE 11

Preparation of methyl 4,7β-dimethyl-3-oxo-4-aza-5α-cholan-24-oate (13)

Methyl 4,7β-dimethyl-3-oxo-4-azachol-5-en-24-oate (12) (56 mg) was hydrogenated at atmospheric pressure and room temperature with $PtO_2$ (6 mg) in HOAc (1.5 ml). After 16 hrs the catalyst was filtered and washed with HOAc (3 times). The HOAc solution was poured carefully into excess 10% $Na_2CO_3$ and extracted with $CH_2Cl_2$ (4 times). The combined extracts were washed with $H_2O$, saturated brine, and dried ($MgSO_4$). Evaporation in vacuo gave 48 mg of 13. NMR ($CDCl_3$): δ0.69 (s, 3H, 18-Me); 0.85 (s, 3H, 19-Me); 0.93 (d, 3H, 20-Me); 1.05 (d, 3H, 7-Me); 2.93 (s, 3H, 4-Me); 3.03 (dd, 1H, 5-H); 3.66 (s, 3H, $CO_2Me$).

EXAMPLE 12

Preparation of
4,7⊖-dimethyl-3-oxo-4-aza-5α-cholan-24-oic acid
(14)

A mixture of methyl 4,7β-dimethyl-3-oxo-4-aza-5α-cholan-24-oate (13) (48 mg), 5N NaOH (1 ml) and MeOH (4 ml) was warmed at 50° for 2 hrs in a $N_2$ atmosphere. Most of the MeOH was removed in vacuo, and the residue was dissolved in $H_2O$ (50 ml) and extracted with $Et_2O$ (2 times). The aqueous phase was acidified with 2N HCl, and the cloudy suspension was extracted with $CH_2Cl_2$ (3 times). The combined extracts were washed with $H_2O$ and saturated brine and dried ($MgSO_4$). Evaporation in vacuo gave 45 mg of 14 as a colorless solid, mp 245°–48°. NMR ($CDCl_3$ plus a little $CD_3OD$): δ0.70 (s, 3H, 18-Me); 0.85 (s, 3H, 19-Me); 0.95 (d, 3H, 20-Me); 1.06 (d, 3H, 7-Me); 2.93 (s, 3H, 4-Me); 3.04 (dd, 1H, 5-H).

EXAMPLE 13

Monkeys and dogs are dosed intravenously with [$^3H$]4,7β-dimethyl-4-aza-5α-cholestan-3-one. The radioactive cholanic acid metabolite is isolated from feces after exhaustive solvent extractions followed by repetitive HPLC and thin layer chromatograpic purifications. This metabolite is also detected in plasma of rats, dogs and monkeys.

Further, 7β-methyl-3-oxo-4-aza-5α-cholan-24-oic acid is observed in monkey feces and the taurine derivative, 4,7β-dimethyl-3-oxo-N-(2-sulfoethyl)-4-aza-5α-cholan-24-amide is observed in rat bile.

What is claimed is:
1. A compound of the Formula I

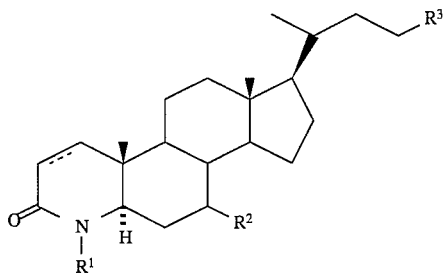

wherein:
the dotted line indicates that a double bond may be present or absent;
$R^1$ is H, methyl or ethyl;
$R^2$ is α- or β-$C_{1-10}$ straight or branched alkyl;
$R^3$ is $CO_2H$ or $CO_2R^4$;
$R^4$ is H, $C_{1-10}$ straight or branched alkyl, aryl, or aralkyl;
Aryl is phenyl, substituted phenyl, naphthyl, or biphenyl; and
Aralkyl is $C_{1-10}$ alkyl substituted with one to three phenyl or substituted phenyl moieties;
or a pharmaceutically acceptable salt thereof.

2. A pharmaceutical composition comprising an effective amount of a compound of claim 1 in a pharmaceutically acceptable carrier.

3. A compound according to claim 1 selected from the group consisting of:
7-methyl-3-oxo-4-aza-5α-cholan-24-oic acid,
7-methyl-3-oxo-4-aza-5α-chol-1-en-24-oic acid,
7-ethyl-3-oxo-4-aza-5α-chol-1-en-24-oic acid,
4,7-dimethyl-3-oxo-4-aza-5α-cholan-24-oic acid,
4-ethyl-7-methyl-3-oxo-4-aza-5'-chol-24-oic acid,
phenyl 7-methyl-3-oxo-4-aza-5α-cholan-24-oate,
2-methoxyphenyl 4,7-dimethyl-3-oxo-4-aza-5α-cholan-24-oate, and
1,1-dimethylethyl 7-methyl-3-oxo-4-aza-5α-chol-1-en-24-oate.

4. A pharmaceutical composition according to claim 1 comprising an effective amount of 4,7β-dimethyl-3-oxo-4-aza-5α-cholan-24-oic acid.

5. A method for treatment of a condition due to an excess of DHT, said condition selected from the group consisting of: androgenic alopecia, acne vulgaris, seborrhea, female hirsutism, benign prostatic hyperplasia, and prostatic cancer comprising the step of administering to an animal a therapeutically effective amount of a compound of claim 1.

6. The method according to claim 5 wherein the treatment is for acne vulgaris.

7. A method for the treatment of a condition due to an excess of DHT, said condition selected from the group consisting of: androgenic alopecia, acne vulgaris, seborrhea, female hirsutism, benign prostatic hyperplasia, and prostatic cancer comprising the step of administering to an animal a therapeutically effective amount of a compound of claim 1 and 4,7β-dimethyl-4-aza-5α-cholestan-3-one.

8. A pharmaceutical composition comprising an effective amount of a compound of claim 3 in a pharmaceutically acceptable carrier.

9. A method according to claim 5 wherein the compound is selected from the group consisting of:
7-methyl-3-oxo-4-aza-5α-cholan-24-oic acid,
7-methyl-3-oxo-4-aza-5α-chol-1-en-24-oic acid,
7-ethyl-3-oxo-4-aza-5α-chol-1-en-24-oic acid,
4,7-dimethyl-3-oxo-4-aza-5α-cholan-24-oic acid,
4-ethyl-7-methyl-3-oxo-4-aza-5α-chol-24-oic acid,
phenyl 7-methyl-3-oxo-4-aza-5α-cholan-24-oate,
2-methoxyphenyl 4,7-dimethyl-3-oxo-4-aza-5α-cholan-24-oate, and
1,1-dimethylethyl 7-methyl-3-oxo-4-aza,5α-chol-1-en-24-oate.

* * * * *